(12) United States Patent
Liu et al.

(10) Patent No.: US 11,578,342 B2
(45) Date of Patent: Feb. 14, 2023

(54) **RECOMBINANT *BACILLUS SUBTILIS* FOR SYNTHESIZING GDP-L-FUCOSE AND APPLICATION THEREOF**

(71) Applicants: BRIGHT DAIRY & FOOD CO., LTD., Shanghai (CN); Jiangnan University, Wuxi (CN)

(72) Inventors: Long Liu, Wuxi (CN); Jian Chen, Wuxi (CN); Guocheng Du, Wuxi (CN); Jieying Deng, Wuxi (CN); Chunmei Chen, Wuxi (CN); Xueqin Lv, Wuxi (CN); Jianghua Li, Wuxi (CN)

(73) Assignees: BRIGHT DAIRY & FOOD CO., LTD., Shanghai (CN); Jiangnan University, Wuxi (CN)

( * ) Notice: Subject to any disclaimer, the term of this patent is extended or adjusted under 35 U.S.C. 154(b) by 423 days.

(21) Appl. No.: 16/747,328

(22) Filed: Jan. 20, 2020

(65) Prior Publication Data
US 2020/0140895 A1    May 7, 2020

(30) Foreign Application Priority Data
Jan. 30, 2019 (CN) .......................... 201910093694.0

(51) Int. Cl.
| | | |
|---|---|---|
| *C12N 15/90* | (2006.01) | |
| *C12P 19/32* | (2006.01) | |
| *C12N 5/00* | (2006.01) | |
| *C12N 1/20* | (2006.01) | |
| *C12R 1/125* | (2006.01) | |

(52) U.S. Cl.
CPC .............. *C12N 15/90* (2013.01); *C12N 1/205* (2021.05); *C12N 5/0031* (2013.01); *C12P 19/32* (2013.01); *C12N 2500/12* (2013.01); *C12N 2500/32* (2013.01); *C12N 2500/74* (2013.01); *C12R 2001/125* (2021.05)

(58) Field of Classification Search
CPC ......... C12N 9/93; C12N 9/0008; C12P 19/26; C12Y 101/01037; C12Y 101/01041; C12Y 102/07001; C12Y 102/07006; C12Y 118/06001; C12Y 604/01001
See application file for complete search history.

(56) References Cited

U.S. PATENT DOCUMENTS 9,868,970 B2 *  1/2018  Liu ...................... C12N 9/93
2017/0145401 A1 *  5/2017  Liu ................ C12Y 305/01001

FOREIGN PATENT DOCUMENTS

WO     WO-2018077892 A1 *  5/2018  ............. C07K 14/24

OTHER PUBLICATIONS

Zhai Y et al. Enhancing GDP-fucose production in recombinant *Escherichia coli* by metabolic pathway engineering. 2015. Enzyme and Microbial Technology. 69:38-45. (Year: 2015).*

* cited by examiner

*Primary Examiner* — Paul J Holland
(74) *Attorney, Agent, or Firm* — IPro, PLLC (57) ABSTRACT

The disclosure discloses recombinant *Bacillus subtilis* for synthesizing guanosine diphosphate fucose and a construction method and application thereof. The recombinant *Bacillus subtilis* is obtained by intensively expressing guanylate kinase and nucleotide diphosphokinase genes and expressing exogenous fucokinase and phosphate guanylyltransferase genes in a genome of *Bacillus subtilis* 168. According to the disclosure, a bacterial strain for synthesizing the guanosine diphosphate fucose is obtained by reconstructing the *Bacillus subtilis* 168, with a volume of intracellular accumulation up to 196.15 g/L. According to the disclosure, by intensively expressing the guanylate kinase and nucleotide diphosphokinase genes, and enhancing the supply of intracellular GDP-L-fucose composition cofactors, the synthesis of the guanosine diphosphate fucose is promoted. The construction method for the recombinant *Bacillus subtilis* of the disclosure is simple and convenient to use, thus having good application prospects.

10 Claims, 3 Drawing Sheets

Specification includes a Sequence Listing.

RECOMBINANT *BACILLUS SUBTILIS* FOR SYNTHESIZING GDP-L-FUCOSE AND APPLICATION THEREOF

The instant application contains a Sequence Listing in ASCII format as a file named seq.txt, created on May 19, 2022, of 25 kB in size, which is hereby incorporated by reference in its entirety.

TECHNICAL FIELD

The disclosure relates to recombinant *Bacillus subtilis* for synthesizing GDP-L-fucose and application thereof, which belongs to the technical field of genetic engineering.

BACKGROUND

Human milk contains important nutritional ingredients, bioactivators and factors for stimulating the growth of intestinal flora. Human milk oligosacchrides (hMOs) play a key role in a lot of physiological functions, i.e., promoting the growth of Bifidobacteria, inhibiting pathogen infection and improving immunoreaction. Due to physiological functions, such as the ability to serve as receptor analogues of enteropathogenic bacteria, the ability to promote immuno-regulation and the ability to reduce inflammation, fucosylated oligosacchrides (FOSs) in the human milk oligosacchrides have gained extensive attention. As FOSs are produced from fucosylation by fucosyltransferase catalysis, guanosine diphosphate fucose (GDP-L-fucose) needs to be used as a donor for fucosyl. With the higher and higher attention to FOSs, many pharmaceuticals companies try to synthesize enough GDP-L-fucose efficiently with chemical methods and biological methods. For chemical efficient synthesis of the GDP-L-fucose, with L-fucopyranosyl tetracetic acid as a starting material, a chemical reaction is initiated by HBr, $Ag_2CO_3$, N-dibenzyl tetrabutylammonium phosphate and other substances. The GDP-L-fucose is a precursor of colanic acid, and colanic acid is a main ingredient of Gram-negative bacterium cytoderm, so some intestinal bacteria, such as *Escherichia coli* and *Salmonella* can be synthesized into the GDP-L-fucose in vivo efficiently. There are two metabolic pathways to synthesize the GDP-L-fucose efficiently biologically: a salvage pathway and a de novo pathway.

The salvage pathway is found in the metabolic pathway of human, in which exogenous fucose is transferred into a cell, and ATP phosphorylated (EC 2.7.1.52) is consumed by fucokinase to form fucose-1-phosphoric acid (Fuc-1-P). The GDP-L-fucose is generated by the Fuc-1-P in combination with guanosine triphosphate (GTP) under the catalysis of L-fucose-1-phosphate guanylyltransferase (EC 2.7.7.30). The de novo pathway for efficient synthesis is commonly found in prokaryotes and eukaryotes, in which the GDP-L-fucose is efficiently synthesized from GDP-mannose under the catalysis of guanosine diphosphate-D-mannose dehydrogenase (GMD, EC4.2.1.47) and GDP-L-fucose synthase (WCAG, EC 1.1.1.271).

*Bacillus subtilis* is a production host which is widely used as food enzyme preparations and important nutrient chemicals, and products thereof are certified as the generally regarded as safe (GRAS) security level.

Therefore, how to synthesize the guanosine diphosphate fucose from the *Bacillus subtilis* with a biological method is still the problem to be solved in the field.

SUMMARY

In order to solve the technical problem, the disclosure aims to provide recombinant *Bacillus subtilis* for synthesizing guanosine diphosphate fucose and a construction method and application thereof. The constructed recombinant *Bacillus subtilis* can be used to synthesize the guanosine diphosphate fucose.

Particularly, according to a first aspect, the disclosure provides recombinant *Bacillus subtilis* which is obtained by intensively expressing guanylate kinase and nucleotide diphosphokinase genes and expressing exogenous fucokinase and phosphate guanylyltransferase genes in a genome of *Bacillus subtilis* 168.

Figure 1:
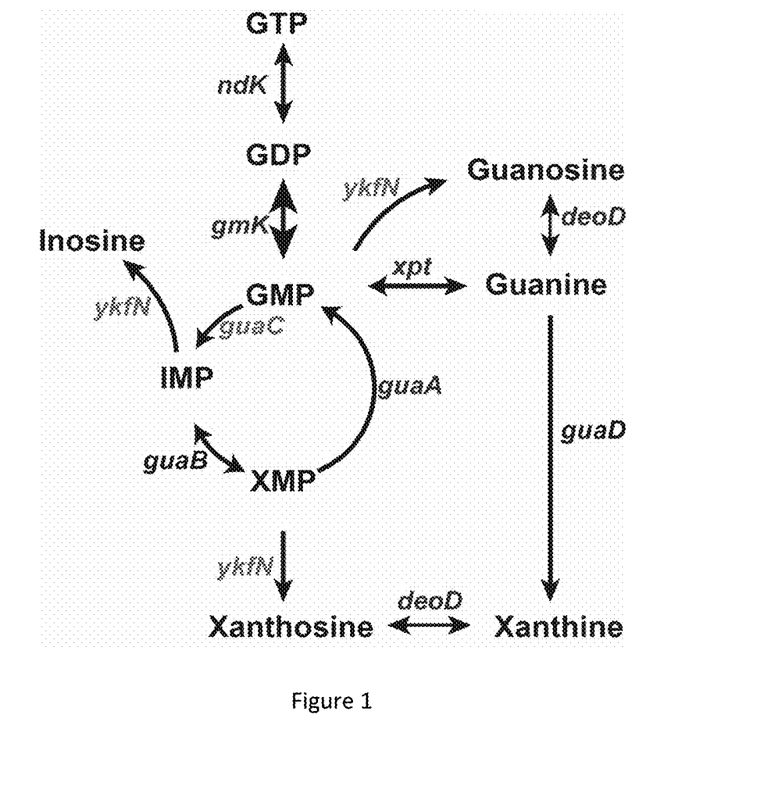
FIG. 1 is a schematic diagram of a reaction in which GTP participates during the synthesis of guanosine diphosphate fucose of the disclosure.

The disclosure provides a method for promoting *Bacillus subtilis* for synthesizing guanosine diphosphate fucose by intensively expressing guanylate kinase and nucleotide diphosphokinase genes. As GTP and ATP are needed to provide energy and GDP groups in a process of synthesizing GDP-L-fucose through the salvage pathway, an enzymatic reaction direction moves towards a GTP direction in reversible reactions from GMP to GDP and from GDP to GTP, but the reaction speed is limited by the expression intensity of guanylate kinase and nucleotide diphosphokinase, as shown in FIG. 1. According to the disclosure, the guanylate kinase (gmk) and nucleotide diphosphokinase (ndk) genes in a genome are enhanced, so that the transformation efficiency from guanosine monophosphate (GMP) to guanosine triphosphate (GTP) is improved, the intracellular supply of GTP is enhanced and the accumulation of the guanosine diphosphate fucose is promoted.

Further, guanylate kinase and nucleotide diphosphokinase genes are intensively expressed by substituting a P43 promoter with promoters of guanylate kinase and nucleotide diphosphokinase genes in the *Bacillus subtilis* 168.

Further, the guanylate kinase gene is shown as a gene with Gene ID: 938821 on NCBI (SEQ ID NO:4), and the nucleotide diphosphokinase gene is shown as a gene with Gene ID: 938997 on NCBI (SEQ ID NO:5), which sequences are hereby incorporated by reference in their entirety for all purposes.

Further, the fucokinase and phosphate guanylyltransferase gene are fkp genes derived from *Bacteroides fragilis*.

According to a second aspect, the disclosure further provides a construction method for the recombinant *Bacillus subtilis* for synthesizing guanosine diphosphate fucose, including the following steps of:

(1) constructing a substitution frame containing upstream and downstream sequences of guanylate kinase and nucleotide diphosphokinase genes, a $P_{43}$ promoter and an actinospectacin resistance gene sequence, transforming the constructed substitution frame into recombinant *Bacillus subtilis* 168, and verifying to confirm that guanylate kinase and nucleotide diphosphokinase are intensively expressed successfully to obtain recombinant *Bacillus subtilis* BSGN; and (2) constructing a recombinant plasmid containing fucokinase and phosphate guanylyltransferase genes, transforming the constructed recombinant plasmid into the *Bacillus subtilis* BSGN and verifying to confirm that fucokinase and phosphate guanylyltransferase are expressed successfully to obtain recombinant *Bacillus subtilis* BSGNF.

Further, in step (1), a sequence of the substitution frame is shown as SEQ ID NO. 1 and SEQ ID NO. 2.

Further, in step (1), the constructed substitution frame is electrically transformed into competent cells of the *Bacillus subtilis* 168.

Further, in step (2), a sequence of the recombinant plasmid is shown as SEQ ID NO. 3.

According to a third aspect, the disclosure provides application of the recombinant *Bacillus subtilis* for synthesizing guanosine diphosphate fucose, where the recombinant *Bacillus subtilis* is applied for fermentation to generate the guanosine diphosphate fucose.

Further, the fermentation is to inoculate a recombinant bacillus seed solution into a fermentation medium in an inoculum size with OD value of 0.1 to 0.3, and culture at 35 to 40° C. and 200 to 250 rpm for 18 to 20 h.

The disclosure has the beneficial effects that the recombinant *Bacillus subtilis* of the disclosure is obtained by intensively expressing the guanylate kinase and nucleotide diphosphokinase genes and expressing the fucokinase and phosphate guanylyltransferase genes on the basis of the *Bacillus subtilis* 168, and a bacterial strain used to synthesize the guanosine diphosphate fucose is obtained through reconstruction, with a volume of intracellular accumulation up to 196.15 g/L. According to the disclosure, by intensively expressing the guanylate kinase and nucleotide diphosphokinase genes, and enhancing the supply of an intracellular GDP-L-fucose composition cofactor GTP, the synthesis of the guanosine diphosphate fucose is promoted. The construction method for the recombinant *Bacillus subtilis* of the disclosure is simple and convenient to use, thus having good application prospects.

DETAILED DESCRIPTION

The detailed description will be made to the disclosure in conjunction with embodiments and figures.

Method for measuring guanosine diphosphate fucose:

High performance liquid chromatography (HPLC) detection method: Agilent1200, a VWD detector, a C18 column (250×4.6 mm, 5 μm), a mobile phase A: 20 Mm of triethylamine acetate buffer (TEAA) with pH 6.0, and a mobile phase B: acetonitrile, with a flow rate of 0.6 mL/min, a column temperature of 35° C., and a sample introduction volume of 10 μL.

Embodiment 1 Intensive Expression of Guanylate Kinase gmk and Nucleotide Diphosphokinase ndk According to upstream and downstream sequences of guanylate kinase gmk and nucleotide diphosphokinase ndk, a $P_{43}$ promoter and a sequence of an actinospectacin resistance gene of *Bacillus subtilis* (*Bacillus subtilis* 168 purchased from American Type Culture Collection, ATCC No. 27370) published on NCBI, a substitution frame 1 (shown as SEQ ID NO. 1) containing the upstream and downstream sequences of the guanylate kinase gmk, the P43 promoter and the sequence of the actinospectacin resistance gene and a substitution frame 2 (shown as SEQ ID NO. 2) containing the upstream and downstream sequences of the nucleotide diphosphokinase ndk, the P43 promoter and the sequence of the actinospectacin resistance gene are constructed.

The constructed substitution frame 1 is electrically transformed into competent cells of the *Bacillus subtilis* 168, with a volume of addition of substitution frame 1 of 100 to 300 ng and under electrical transformation conditions of a voltage of 2.5 kV and an electric shock reagent of 5 ms. The constructed substitution frame 2 is electrically transformed into the competent cells of the *Bacillus subtilis* 168, with a volume of addition of substitution frame 2 of 100 to 300 ng and under electrical transformation conditions of a voltage of 2.5 kV and an electric shock reagent of 5 ms. Then, the competent cells are recovered at 37° C. for 5 h, coated on a resistant LB plate of actinospectacin with a final concentration of 10 μg/mL and subjected to anaerobic culture at 37° C. for 48 h, and a plurality of monoclones are selected.

As the upper and downstream sequences of the guanylate kinase gmk and the nucleotide diphosphokinase ndk exist in the substitution frames, which are homologous with a transportprotein gene of the *Bacillus subtilis* 168, the P43 promoters in the substitution frames are substituted with promoters of the guanylate kinase gmk and the nucleotide diphosphokinase ndk of the *Bacillus subtilis* 168.

Figure 2:
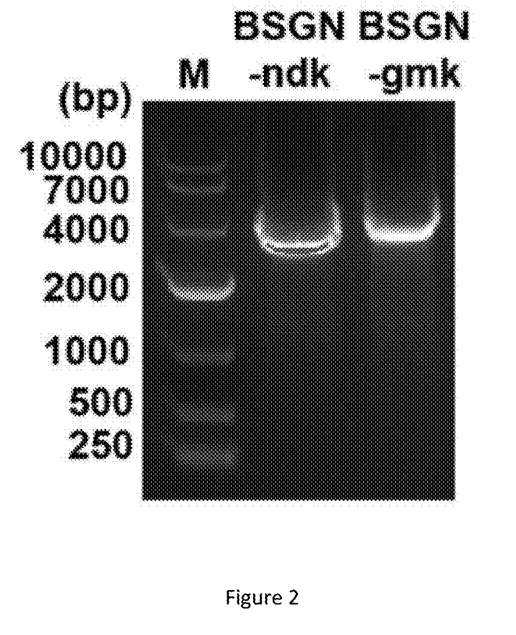
FIG. 2 is an integrated PCR verification agarose gel electrophoretogram of intensively expressed gmk and ndk genes in Embodiment 1 of the disclosure.

Through the screening of the resistant plate of actinospectacin, and colony PCR verification, after sequencing, whether or not the guanylate kinase gmk and the nucleotide diphosphokinase ndk are intensively expressed successfully is confirmed, and one in which the actinospectacin is positive in resistance is the *Bacillus subtilis* with the substitution frame successfully transformed; the agarose gel electrophoretogram is shown in FIG. 2; and one with a special band verified by the colony PCR and consistence between a sequencing result and a theoretical result is the *Bacillus subtilis* with the substitution frame successfully transformed and recombined, i.e., the *Bacillus subtilis* in which the guanylate kinase gmk and the nucleotide diphosphokinase ndk are intensively expressed successfully.

Upon the confirmation of the successful intensive expression of the guanylate kinase gmk and the nucleotide diphosphokinase ndk, recombinant *Bacillus subtilis* BSGN is obtained.

Embodiment 2 Heterogenous Expression of Exogenous Genes of *Bacteroides fragilis*

According to sequences of fucokinase and phosphate guanylyltransferase genes fkp of *Bacteroides fragilis* (ATCC No. 25285) published on NCBI, a recombinant plasmid $pP_{43}$-Fkp with a sequence, shown as SEQ ID NO. 3, is constructed through PCR linear amplification of the genes fkp and a plasmid pP43NMK and connection by one-step clone of ClonExpress II One Step Cloning Kit (Vazyme).

The constructed recombinant plasmid is electrically transformed into the competent cells of the recombinant *Bacillus subtilis* BSGN obtained in Embodiment 1, with a volume of addition of 50 to 300 ng and under electrical transformation conditions of a voltage of 2.5 kV and an electric shock reagent of 5 ms. Then, the competent cells are recovered at 37° C. for 5 h, coated on a resistant LB plate of kanamycin with a final concentration of 10 μg/mL and subjected to anaerobic culture at 37° C. for 48 h, and a plurality of monoclones are selected.

Figure 3:
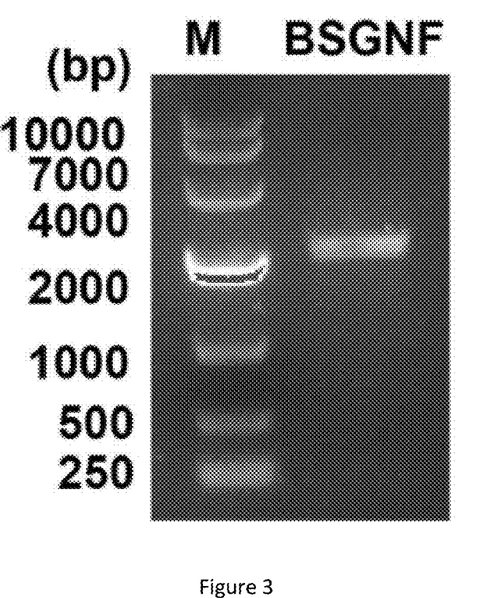
FIG. 3 is a PCR verification agarose gel electrophoretogram of a fkp gene expressed through plasmid transformation in Embodiment 2 of the disclosure.

Through the screening of the kanamycin resistant plate, and colony PCR verification, after sequencing, whether or not the fucokinase and the phosphate guanylyltransferase genes fkp are expressed successfully is confirmed. One in which the kanamycin is positive in resistance is the *Bacillus subtilis* with successful transformation; the agarose gel electrophoretogram is shown in FIG. 3; and one with a special band verified by colony PCR and consistence between a sequencing result and a theoretical result is the *Bacillus subtilis* with successful transformation and recombination, i.e., the fucokinase and the phosphate guanylyltransferase are expressed successfully.

Upon the confirmation of the successful expression of the fucokinase and the phosphate guanylyltransferase of the *Bacteroides fragilis*, recombinant *Bacillus subtilis* BSGNF is obtained.

Embodiment 3 Production of Guanosine Diphosphate Fucose Through Fermentation

The recombinant *Bacillus subtilis* BSGNF is prepared into a seed solution. A formula of a seed solution medium includes 10 g/L tryptone, 5 g/L yeast powder, and 10 g/L NaCl. A method for preparing the seed solution includes: selecting fresh single colonies on a plate, and culturing in the seed medium for 8 to 10 h.

The seed solution is inoculated into a fermentation medium in an inoculum size with OD value of 0.1. A formula of the fermentation medium includes: 20 g/L initial glycerinum, 6 g/L peptone, 12 g/L yeast powder, 6 g/L $(NH_4)SO_4$, 12.5 g/L $K_2HPO_4 \cdot 3H_2O$, 2.5 g/L $KH_2PO_4$, 5 g/L $CaCO_3$ and 10 ml/L microelement solution. The microelement solution contains: 1.0 g/L $MnSO_4 \cdot 5H_2O$, 0.4 g/L $CoCl_2 \cdot 6H_2O$, 0.2 g/L $NaMoO_4 \cdot 2H_2O$, 0.2 g/L $ZnSO_4 \cdot 7H_2O$, 0.1 g/L $AlCl_3 \cdot 6H_2O$, 0.1 g/L $CuCl_2 \cdot H_2O$, 0.05 g/L $H_3BO_4$ and 5 M HCl. The seed solution is cultured at 35° C. and 200 rpm for 18 h.

After fermentation ends, the content of guanosine diphosphate fucose in fermented supernatant fluid is measured through a gas chromatograph-mass spectrometer, a gas chromatograph-mass spectrometer chromatogram of the guanosine diphosphate fucose is shown as FIG. 1, and the content of the measured guanosine diphosphate fucose is up to 196.15 mg/L.

Embodiment 4 Production of Guanosine Diphosphate Fucose Through Fermentation

The recombinant *Bacillus subtilis* BSGNF is prepared into a seed solution. A formula of a seed medium includes: 10 g/L tryptone, 5 g/L yeast powder, and 10 g/L NaCl. A method for preparing the seed solution includes: selecting fresh single colonies on a plate, and culturing in the seed medium for 8 to 10 h.

The seed solution is inoculated into a fermentation medium in an inoculum size with OD value of 0.3, and a formula of the fermentation medium includes: 20 g/L initial glycerinum, 6 g/L peptone, 12 g/L yeast powder, 6 g/L $(NH_4)SO_4$, 12.5 g/L $K_2HPO_4 \cdot 3H_2O$, 2.5 g/L $KH_2PO_4$, 5 g/L $CaCO_3$ and 10 ml/L microelement solution. The microelement solution contains: 1.0 g/L $MnSO_4 \cdot 5H_2O$, 0.4 g/L $CoCl_2 \cdot 6H_2O$, 0.2 g/L $NaMoO_4 \cdot 2H_2O$, 0.2 g/L $ZnSO_4 \cdot 7H_2O$, 0.1 g/L $AlCl_3 \cdot 6H_2O$, 0.1 g/L $CuCl_2 \cdot H_2O$, 0.05 g/L $H_3BO_4$ and 5 M HCl. The seed solution is cultured at 40° C. and 250 rpm for 20 h.

After fermentation ends, the content of guanosine diphosphate fucose in fermented supernatant fluid is up to 187.21 mg/L.

COMPARATIVE EXAMPLE 1

According to upstream and downstream sequences of guanylate kinase gmk and nucleotide diphosphokinase ndk, a $P_{43}$ promoter and a sequence of an actinospectacin resistance gene of *Bacillus subtilis* (*Bacillus subtilis* 168 purchased from American Type Culture Collection, ATCC No. 27370) published on NCBI, a substitution frame 1 (shown as SEQ ID NO. 1) containing the upstream and downstream sequences of the guanylate kinase gmk, the P43 promoter and the sequence of the actinospectacin resistance gene and a substitution frame 2 (shown as SEQ ID NO. 2) containing the upstream and downstream sequences of the nucleotide diphosphokinase ndk, the $P_{43}$ promoter and the sequence of the actinospectacin resistance gene are constructed.

The constructed substitution frame 1 is electrically transformed into competent cells of the *Bacillus subtilis* 168, with a volume of addition of substitution frame 1 of 100 to 300 ng and under electrical transformation conditions of a voltage of 2.5 kV and an electric shock reagent of 5 ms. The constructed substitution frame 2 is electrically transformed into the competent cells of the *Bacillus subtilis* 168, with a volume of addition of substitution frame 2 of 100 to 300 ng and under electrical transformation conditions of a voltage of 2.5 kV and an electric shock reagent of 5 ms. Then, the competent cells are recovered at 37° C. for 5 h, coated on a resistant LB plate of actinospectacin with a final concentration of 10 μg/mL and subjected to anaerobic culture at 37° C. for 48 h, and a plurality of monoclones are selected.

As the upper and downstream sequences of the guanylate kinase gmk and the nucleotide diphosphokinase ndk exist in the substitution frames, which are homologous with a transportprotein gene of the *Bacillus subtilis* 168, the $P_{43}$ promoters in the substitution frames are substituted with promoters of the guanylate kinase gmk and the nucleotide diphosphokinase ndk of the *Bacillus subtilis* 168.

Through the screening of the resistant plate of actinospectacin, and colony PCR verification, after sequencing, whether or not the guanylate kinase gmk and the nucleotide diphosphokinase ndk are intensively expressed successfully is confirmed, and one in which the actinospectacin is positive in resistance is the *Bacillus subtilis* with the substitution frame successfully transformed; and one with a special band verified by colony PCR and consistence between a sequencing result and a theoretical result is the *Bacillus subtilis* in which the substitution frames are successfully transformed and recombined, i.e., the *Bacillus subtilis* in which the guanylate kinase gmk and the nucleotide diphosphokinase ndk are intensively expressed successfully.

Upon the confirmation of the successful intensive expression of the guanylate kinase gmk and the nucleotide diphosphokinase ndk, recombinant *Bacillus subtilis* BSGN is obtained.

Guanosine diphosphate fucose is produced by fermenting the recombinant *Bacillus subtilis* BSGN, with a fermentation condition being same as that in Embodiment 3. After fermentation ends, cells are collected through centrifugation, and an intracellular soluble mixed solution is obtained through ultrasonication, in which the guanosine diphosphate fucose is not detected.

COMPARATIVE EXAMPLE 2

According to sequences of fucokinase and phosphate guanylyltransferase genes fkp of *Bacteroides fragilis* (ATCC No. 25285) published on NCBI, a recombinant plasmid with a sequence, shown as SEQ ID NO. 3, is constructed.

The constructed recombinant plasmid is electrically transformed into competent cells of the *Bacillus subtilis* 168, with a volume of addition of 50 to 300 ng and under electrical transformation conditions of a voltage of 2.5 kV and an electric shock reagent of 5 ms. Then, the competent cells are recovered at 37° C. for 5 h, coated on a resistant LB plate of kanamycin with a final concentration of 25 μg/mL and subjected to aerobic culture at 37° C. for 12 h, and a plurality of monoclones are selected.

Through the screening of the resistant plate of e kanamycin, and colony PCR verification, after sequencing, whether or not the fucokinase and phosphate guanylyltransferase genes are expressed successfully is confirmed, and one in which the kanamycin is positive in resistance is the *Bacillus subtilis* with successful transformation; and one with a special band verified by colony PCR and consistence between a sequencing result and a theoretical result is the *Bacillus subtilis* in which substitution frames are successfully recombined, i.e., the fucokinase and the phosphate guanylyltransferase are expressed successfully.

Upon the confirmation of the successful expression of the fucokinase and the phosphate guanylyltransferase of the *Bacteroides fragilis*, recombinant *Bacillus subtilis* BSF is obtained.

Guanosine diphosphate fucose is produced by fermenting the recombinant *Bacillus subtilis* BSF, with a fermentation condition being same as that in Embodiment 3. After fermentation ends, cells are collected through centrifugation, and an intracellular soluble mixed solution is obtained through ultrasonication, in which the guanosine diphosphate fucose is not detected.

The foregoing description is only preferred embodiments of the disclosure, and is not intended to limit the disclosure. All any modifications, equivalent replacement and simple improvement and the like within the spirit and principles of the disclosure should be included within protection scope of the disclosure.

What is claimed is:

1. A recombinant *Bacillus subtilis* 168 expressing a guanylate kinase gene and a nucleotide diphosphokinase gene, wherein an exogenous fucokinase gene, and an exogenous phosphate guanylyltransferase gene are expressed in the genome of the recombinant *Bacillus subtilis* 168, and wherein the guanylate kinase gene and nucleotide diphosphokinase gene are expressed by substituting a P43 promoter of the recombinant *Bacillus subtilis* 168 with promoters of the guanylate kinase gene nucleotide diphosphokinase gene from *Bacillus subtilis* 168.

2. The recombinant *Bacillus subtilis* 168 of claim 1, wherein the guanylate kinase gene comprises the nucleotide sequence of SEQ ID NO: 4, and the nucleotide diphosphokinase gene comprises the nucleotide sequence of SEQ ID NO: 5.

3. The recombinant *Bacillus subtilis* 168 of claim 1, wherein the fucokinase gene and the phosphate guanylyltransferase gene are fkp genes derived from *Bacteroides fragilis*.

4. The recombinant *Bacillus subtilis* 168 of claim 3, wherein the fkp gene is expressed by expression vector pP43NMK.

5. The recombinant *Bacillus subtilis* 168 of claim 4, wherein the fkp gene is ligated into expression vector pP43NMK, and the expression vector pP43NMK after ligation comprises the nucleotide sequence of SEQ ID NO: 3.

6. A method for generating guanosine diphosphate fucose comprising incubating the recombinant *Bacillus subtilis* 168 of claim 1 in a medium comprising fucose to undergo fermentation in a fermentation medium.

7. The method of claim 6, wherein the method further comprises inoculating a seed solution comprising the recombinant *Bacillus subtilis* 168 into the fermentation medium in an inoculum size with OD value of 0.1 to 0.3, and culturing at 35° C. to 40° C., 200 rpm to 250 rpm, and for 18 hours to 20 hours.

8. The method of claim 6, wherein the fermentation further comprises inoculating the recombinant *Bacillus subtilis* 168 into a seed medium and culturing for 8 hours to 10 hours.

9. The method of claim 8, wherein the seed medium contains 10 g/L of tryptone, 5 g/L of yeast powder, and 10 g/L of NaCl.

10. The method of claim 6, wherein the fermentation medium comprises: 20 g/L of glycerinum, 6 g/L of peptone, 12 g/L of yeast powder, 6 g/L of $(NH_4)SO_4$, 12.5 g/L of $K_2HPO_4*3H_2O$, 2.5 g/L of $KH_2PO_4$, 5 g/L of $CaCO_3$, and 10 ml/L of microelement solution; and wherein the microelement solution comprises: 1.0 g/L of $MnSO_4*5H_2O$, 0.4 g/L of $CoCl_2*6H_2O$, 0.2 g/L of $NaMoO_4*2H_2O$, 0.2 g/L of $ZnSO_4*7H_2O$, 0.1 g/L of $AlCl_3*6H_2O$, 0.1 g/L of $CuCl_2*H_2O$, 0.05 g/L of $H_3BO_4$, and 5M of HCl.

* * * * *

SEQUENCE LISTING

```
<160> NUMBER OF SEQ ID NOS: 5

<210> SEQ ID NO 1
<211> LENGTH: 4042
<212> TYPE: DNA
<213> ORGANISM: Artificial Sequence
<220> FEATURE:
<223> OTHER INFORMATION: Synthetic DNA

<400> SEQUENCE: 1
ggcttgaaat tgattggccg ctgctcgatg agtttgtcgc agccgcgaga gatatgaaga      60
agcggtatca attgtctgca gagcccgatg taatggattt ctttaagctt gatcatgtcg     120
tccaggttca tgaagaacag acgcaaaatg acaagctgga ggcgttgatc atcgatgctg     180
cagaagaagc ggtaaaaggt ctctgtgaaa tgcgtgaaaa agaggggctg ctcttagcga     240
aagactgcct gatgcatatt gatcagcttg aagagctggt gagagaaact gaattgctgg     300
ctgcagatgt cgtatctcgt taccgggaac ggctgtatgc cagaatcaaa gaatggactg     360
aagacgtatt agacgagagc cggcttgtaa cagaatgcgc tatttttgca gaccgctctg     420
atatcactga agagattaca aggctgaaga gccacttcgc ccagtttcgt gatatattag     480
ctagtggcgg agctgtcggg cgcaaactcg actttcttgt tcaggagctc aatcgggaag     540
caaatacgat cggctcaaaa gcaaatgatc atcagatcac aaagcttgtc gttgaaatga     600
aaagttctat tgaaaaaata aaagaacaag tgcaaaatat agaatagtga ctgtgcgtat     660
tgtttacaga cggtcttact aggctaaact agagacgtct attttacagg gggaacgtag     720
aagatgacga ttaaactgat taatatcgga tttggcaata tcatctccgc caatcggatg     780
atttcgattg tcagcccgga gtctgcgcca atcaaacgga tgattcagga tgcaagagac     840
cgcggaatgc taattgacgc tacatacgga cgaagaaccc gtgcagttgt cgtcatggat     900
agtgatcaca ttatcttatc tgccgtccag cctgagacag ttgcacacag actttctgtt     960
aaagaagaaa ttatggatga agggcagggg taattgccgc tacccgggga tcctctagag    1020
attgtaccgt tcgtatagca tacattatac gaagttatcg attttcgttc gtgaatacat    1080
gttataataa ctataactaa taacgtaacg tgactggcaa gagatatttt taaaacaatg    1140
aataggttta cacttacttt agtttatgg aaatgaaaga tcatatcata tataatctag    1200
aataaaatta actaaaataa ttattatcta gataaaaaat ttagaagcca atgaaatcta    1260
taaataaact aaattaagtt tatttaatta acaactatgg atataaaata ggtactaatc    1320
aaaatagtga ggaggatata tttgaataca tacgaacaaa ttaataaagt gaaaaaaata    1380
cttcggaaac atttaaaaaa taaccttatt ggtacttaca tgtttggatc aggagttgag    1440
agtggactaa aaccaaatag tgatcttgac tttttagtcg tcgtatctga accattgaca    1500
```

```
gatcaaagta aagaaatact tatacaaaaa attagaccta tttcaaaaaa aataggagat      1560
aaaagcaact tacgatatat tgaattaaca attattattc agcaagaaat ggtaccgtgg      1620
aatcatcctc ccaaacaaga atttatttat ggagaatggt tacaagagct ttatgaacaa      1680
ggatacattc ctcagaagga attaaattca gatttaacca taatgcttta ccaagcaaaa      1740
cgaaaaaata aaagaatata cggaaattat gacttagagg aattactacc tgatattcca      1800
ttttctgatg tgagaagagc cattatggat tcgtcagagg aattaataga taattatcag      1860
gatgatgaaa ccaactctat attaacttta tgccgtatga ttttaactat ggacacgggt      1920
aaaatcatac caaagatat tgcgggaaat gcagtggctg aatcttctcc attagaacat      1980
agggagagaa ttttgttagc agttcgtagt tatcttggag agaatattga atggactaat      2040
gaaaatgtaa atttaactat aaactattta aataacagat taaaaaaatt ataaataact      2100
tcgtatagca tacattatac gaacggtaga atcgtcgact gataggttgg tgtggttggt      2160
gataggtggt atgttttcgc ttgaactttt aaatacagcc attgaacata cggttgattt      2220
aataactgac aaacatcacc ctcttgctaa agcggccaag gacgctgccg ccggggctgt      2280
ttgcgttttt gccgtgattt cgtgtatcat tggtttactt attttttttgc caaagctgta      2340 atggctgaaa attcttacat ttatttttaca ttttagaaa tgggcgtgaa aaaaagcgcg      2400
cgattatgta aaatataaag tgatagcatg aaagaaagag ggttattaat cgttctctca      2460
ggtccctcag gagttggtaa aggaacggtt cgacaagcga tcttttcgca ggaagacaca      2520
aaatttgaat attcgatttc agtaaccaca agaagtccaa gagagggcga agtgaacgga      2580
gtcgattatt ttttcaaaac aagagacgaa ttcgagcaaa tgattgcgga caacaagctg      2640
cttgaatggg cagagtatgt cggcaattat tacggcacgc cagtcgatta tgttgaacag      2700
acgcttcaag atggaaaaga cgtcttttta gaaattgaag ttcaaggggc tcttcaagtg      2760
agaaatgctt ccccggaagg cctgtttatt ttccttgcgc ctccaagcct ttctgaactg      2820
aaaaacagaa tcgtgacacg aggaacgaaa acagacgctc tgattgaaaa tcgaatgaaa      2880
gccgcaaaag ctgagatcga aatgatggat gcttatgact atgtcgttga aaacgataat      2940
gtcgaaacgg cttgcgataa aatcaaagca atcgttcttg ctgaacattt gaagcgtgaa      3000
cgcgttgcac caagatataa gaaaatgctg gaggttgaat aatcaatgtt agatccgtca      3060
attgattctt taatgaataa attagattca aaatatacgc tggtgactgt ttctgcgaga      3120
cgtgcccgtg aaatgcaaat caaaaagac caaatgattg aacatacgat ttcacacaaa      3180
tatgtaggca aagctttaga agaaattgat gcaggcctgc tttcgtttga aaggaagac      3240 cgcgaatagt agcacaagta gcaacctata tcatgtaggt tgttattttt ttccgtgcgg      3300
ttttgtaaag tgcagagggg gagaattcat tgcttaacaa tcgaaatgtg ttactttgcg      3360
tgagtggagg catcgctgtt tataaagcct gtgcgttaac gagcaagctg gttcaggcag      3420
gagcaaatgt caaagtgatt atgactgaat ccgcttgccg attcgtttca ccgctgacat      3480
ttcaggcatt gagccgccac gaagtctata cagatacatt taaagaacaa aatccaagcg      3540
tcatttctca tattgatgcc gcagactggg ccgacttgat tatcgtagcg ccggctacgg      3600
ctaatgtgat tggaaaactg gcaaacggca tcgctgatga tatgctgacg acaacattgt      3660
tggcagcaac ggctcccgtt tggatcgcgc cggcaatgaa cgttcatatg tatgaccacc      3720
cggcagtcaa acgaaacatt tctgttcttt atcaggacgg ttattgtttt attgagccaa      3780
gtgagggcta tttagcatgc ggttacgtag gaaaaggcag attggaagag ccggaaaaca      3840
tcgtaaagct ggccgaaaaa cattttgctg aagaaacatc cgctcccttta gaaggcaagc      3900
```

| | |
|---|---|
| atgtggtcat tacagccggc ccaacgcggg aagcgattga tcctgtccgg ttttttacca | 3960 |
| ataaatcgac gggcaaaatg ggctacgcac tggcggaggc tgctgttcag ctcggcgcac | 4020 |
| gggtaatctt aatttctggg cc | 4042 |

<210> SEQ ID NO 2
<211> LENGTH: 4447
<212> TYPE: DNA
<213> ORGANISM: Artificial Sequence
<220> FEATURE:
<223> OTHER INFORMATION: Synthetic DNA

<400> SEQUENCE: 2

| | |
|---|---|
| tccgattacc cgcttttaag cgaggcaggt cttcacctgc tgcaggccgg agggaaacgt | 60 |
| attcggcctg ttttcgtgct gctttctggc atgtttggcg attatgatat taataagatt | 120 |
| aaatatgtcg ccgtcactct ggaaatgatt cacatggcat ctttggttca tgatgatgtc | 180 |
| attgatgatg cagagcttcg ccgaggaaaa ccgacaatca agcaaagtg gacaatcgt | 240 |
| attgcgatgt acacaggcga ttatatgctt gcgggatctc ttgaaatgat gacgagaatt | 300 |
| aacgaaccga agcccatag gattttgtca cagacgatcg ttgaagtttg tctaggggaa | 360 |
| attgagcaga tcaaagacaa atacaacatg gaacaaaatc tcagaacgta tctccgccgt | 420 |
| atcaaaagaa aaacagctct cttgatcgcg gtcagctgcc agcttggtgc cattgcgtct | 480 |
| ggagctgatg agaagattca taaggcattg tactggtttg ggtattacgt cggcatgtct | 540 |
| tatcagatta ttgatgatat tcttgatttt acttcaactg aggaagagct gggtaaaccc | 600 |
| gtaggaggag atttgcttca aggaaacgtc acattgccag tgctgtatgc cctgaaaaat | 660 |
| cctgcattaa aaaccagct taaattgatt aacagtgaga caacgcagga acagcttgaa | 720 |
| ccaatcattg aagaaatcaa aaaaacagat gcaattgaag catctatggc agtaagcgaa | 780 |
| atgtatctgc agaaagcttt tcagaaatta aacacgcttc ctcgagggcg cgcacgctcg | 840 |
| tctcttgcag ccatcgcaaa atatatcggt aaaagaaaat tttaattttt gtagatatta | 900 |
| agaaatttct ccgccccgga ttgattaatt atcagaaaga tgttacgatt tcggtgtgca | 960 |
| gtgtgaaagc ctatacatac ataatgatgg ggtggagaat atgatggaaa agactttat | 1020 |
| catggtgaaa ccagacggtg tccaacgtca gctcattggg gacattttat ctagattcga | 1080 |
| acgtaagggc ttcaattag ctggcgccaa gttaatgaga gtgactgaac aaatggctga | 1140 |
| gaaacactac gccgaacatc aaggtaagcc tttcttcgga gagctcgttg agtttattac | 1200 |
| ttcaggacct gtattcgcaa tggtgtggga aggcgaaaat gtcattgaag tgacgagaca | 1260 |
| gctgatcggg aaaacaaacc ctaaagaagc tttacctggt acgattcgtg gggattatgg | 1320 |
| catgtttgtc ggaaaaaaca tcatccacg ctctgattct ctcgaaagtg cagaacgcga | 1380 |
| gattaacatt ttctttaaga atgaagaatt agtatcatat cagcagctta tggcaggctg | 1440 |
| gatctattaa tcattgtgaa aataagcaac agagccggca acatataacg ccgccggttt | 1500 |
| ttgttctgtt ttgtaaaggt ttacattaaa gtgaataaag ggttgaatgg cagtgtgcat | 1560 |
| cagacctctg cctttcccaa cgatctaaaa tcagctgaaa agctgatttt tttattgaaa | 1620 |
| caatacaatt tcctgataaa acaagctata ctaggacaaa aagacagcga gactgggaga | 1680 |
| gtagagatgg atacatacag cgtatttaca acgaaatgga acaattaac cggagtcgat | 1740 |
| ttaacactat ataagaagc acaaatgaag agaaggctaa cgtcacttta tgagaaaaag | 1800 |
| gggttccaaa gctttaagga ctttgctgcg gcattggaaa aggatcaagc tctcttaaat | 1860 |

-continued

```
gaaacattgg acagaatgac gatcaatgtt tcagaatttt atcgtaatta taaaagatgg    1920
gaagttcttg agactgcaat tctgccgtta atcaagacct ctaggccttt aaaaatttgg    1980
agtgccgcct gctcaacggg tacccgggga tcctctagag attgtaccgt tcgtatagca    2040
tacattatac gaagttatcg attttcgttc gtgaatacat gttataataa ctataactaa    2100
taacgtaacg tgactggcaa gagatatttt taaaacaatg aataggttta cacttacttt    2160
agttttatgg aaatgaaaga tcatatcata tataatctag aataaaatta actaaaataa    2220
ttattatcta gataaaaaat ttagaagcca atgaaatcta taaataaact aaattaagtt    2280
tatttaatta caactatgg atataaaata ggtactaatc aaaatagtga ggaggatata    2340
tttgaataca tacgaacaaa ttaataaagt gaaaaaaata cttcggaaac atttaaaaaa    2400
taaccttatt ggtacttaca tgtttggatc aggagttgag agtggactaa accaaaatag    2460
tgatcttgac tttttagtcg tcgtatctga accattgaca gatcaaagta aagaaatact    2520
tatacaaaaa attagaccta tttcaaaaaa aataggagat aaaagcaact tacgatatat    2580
tgaattaaca attattattc agcaagaaat ggtaccgtgg aatcatcctc ccaaacaaga    2640
atttatttat ggagaatggt tacaagagct ttatgaacaa ggatacattc ctcagaagga    2700
attaaattca gatttaacca taatgcttta ccaagcaaaa cgaaaaaata aaagaatata    2760
cggaaattat gacttagagg aattactacc tgatattcca ttttctgatg tgagaagagc    2820
cattatggat tcgtcagagg aattaataga taattatcag gatgatgaaa ccaactctat    2880
attaacttta tgccgtatga ttttaactat ggacacgggt aaaatcatac caaaagatat    2940
tgcgggaaat gcagtggctg aatcttctcc attagaacat agggagagaa ttttgttagc    3000
agttcgtagt tatcttggag agaatattga atggactaat gaaaatgtaa atttaactat    3060
aaactattta aataacagat taaaaaaatt ataaataact tcgtatagca tacattatac    3120
gaacggtaga atcgtcgact gataggttgg tgtggttggt gataggtggt atgttttcgc    3180
ttgaactttt aaatacagcc attgaacata cggttgattt aataactgac aaacatcacc    3240
ctcttgctaa agcggccaag gacgctgccg ccggggctgt ttgcgttttt gccgtgattt    3300
cgtgtatcat tggtttactt atttttttgc caaagctgta atggctgaaa attcttacat    3360
ttatttaca ttttagaaa tgggcgtgaa aaaagcgcg cgattatgta aaatataaag     3420
tgatagcaaa ggaggtgaaa tgtacacatg atggaaaaga cttttatcat ggtgaaacca    3480
gacggtgtcc aacgtcagct cattggggac attttatcta gattcgaacg taagggctta    3540
caattagctg gcgccaagtt aatgagagtg actgaacaaa tggctgagaa acactacgcc    3600
gaacatcaag gtaagccttt cttcggagag ctcgttgagt ttattacttc aggacctgta    3660
ttcgcaatgg tgtgggaagg cgaaaatgtc attgaagtga cgagacagct gatcgggaaa    3720
acaaaccta aagaagcttt acctggtacg attcgtgggg attatggcat gtttgtcgga    3780
aaaaacatca tccacggctc tgattctctc gaaagtgcag aacgcgagat taacattttc    3840
tttaagaatg aagaattagt atcatatcag cagcttatgg caggctggat ctattaatca    3900
ttgtgaaaat aagcaacaga gccggcaaca tataacgccg ccggtttttg ttctgttttg    3960
taaaggttta cattaaagtg aataaagggt tgaatggcag tgtgcatcag acctctgcct    4020
ttcccaacga tctaaaatca gctgaaaagc tgattttttt attgaaacaa tacaatttcc    4080
tgataaaaca agctatacta ggacaaaaag acagcgagac tgggagagta gagatggata    4140
catacagcgt atttacaacg aaatggaaac aattaaccgg agtcgattta acactatata    4200
aagaagcaca aatgaagaga aggctaacgt cactttatga gaaaaagggg ttccaaagct    4260
```

```
ttaaggactt tgctgcggca ttggaaaagg atcaagctct cttaaatgaa acattggaca    4320
gaatgacgat caatgtttca gaattttatc gtaattataa agatgggaa gttcttgaga     4380 ctgcaattct gccgttaatc aagacctcta ggcctttaaa aatttggagt gccgcctgct    4440
caacggg                                                              4447

<210> SEQ ID NO 3
<211> LENGTH: 9577
<212> TYPE: DNA
<213> ORGANISM: Artificial Sequence
<220> FEATURE:
<223> OTHER INFORMATION: Synthetic DNA

<400> SEQUENCE: 3
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt ccttaaggaa cgtacagacg     420
gcttaaaagc ctttaaaaac gttttttaagg ggtttgtaga caaggtaaag gataaaacag    480
cacaattcca agaaaacac gatttagaac ctaaaaagaa cgaatttgaa ctaactcata     540
accgagaggt aaaaaaagaa cgaagtcgag atcagggaat gagtttataa aataaaaaaa    600
gcacctgaaa aggtgtcttt ttttgatggt tttgaacttg ttctttctta tcttgataca    660
tatagaaata acgtcatttt tattttagtt gctgaaaggt gcgttgaagt gttggtatgt    720
atgtgtttta aagtattgaa aacccttaaa attggttgca cagaaaaacc ccatctgtta    780
aagttataag tgactaaaca aataactaaa tagatggggg tttcttttaa tattatgtgt    840
cctaatagta gcatttattc agatgaaaaa tcaagggttt tagtggacaa gacaaaaagt    900
ggaaaagtga gaccatggag agaaaagaaa tcgctaatg ttgattactt tgaacttctg     960
catattcttg aatttaaaaa ggctgaaaga gtaaaagatt gtgctgaaat attagagtat    1020
aaacaaaatc gtgaaacagg cgaaagaaag ttgtatcgag tgtggttttg taaatccagg    1080
ctttgtccaa tgtgcaactg gaggagagca atgaaacatg gcattcagtc acaaaaggtt    1140
gttgctgaag ttattaaaca aaagccaaca gttcgttggt gtttctcac attaacagtt    1200 aaaaatgttt atgatggcga agaattaaat aagagtttgt cagatatggc tcaaggattt    1260
cgccgaatga tgcaatataa aaaaattaat aaaaatcttg ttggttttat gcgtgcaacg    1320
gaagtgacaa taaataataa agataattct tataatcagc acatgcatgt attggtatgt    1380
gtggaaccaa cttattttaa gaatacagaa aactacgtga atcaaaaaca atggattcaa    1440
ttttggaaaa aggcaatgaa attagactat gatccaaatg taaagttca atgattcga     1500 ccgaaaaata aatataaatc ggatatacaa tcggcaattg acgaaactgc aaaatatcct    1560
gtaaaggata cggattttat gaccgatgat gaagaaaaga atttgaaacg tttgtctgat    1620
ttggaggaag gtttacaccg taaaaggtta atctcctatg gtggtttgtt aaaagaaata    1680
cataaaaaat taacccttga tgacacagaa gaaggcgatt tgattcatac agatgatgac    1740
gaaaaagccg atgaagatgg atttctatt attgcaatgt ggaattggga acggaaaaat    1800
```

```
tatttttatta aagagtagtt caacaaacgg gccagtttgt tgaagattag atgctataat    1860
tgttattaaa aggattgaag gatgcttagg aagacgagtt attaatagct gaataagaac    1920
ggtgctctcc aaatattctt atttagaaaa gcaaatctaa aattatctga aaagggaatg    1980
agaatagtga atggaccaat aataatgact agagaagaaa gaatgaagat tgttcatgaa    2040
attaaggaac gaatattgga taaatatggg gatgatgtta aggctattgg tgtttatggc    2100
tctcttggtc gtcagactga tgggccctat tcggatattg agatgatgtg tgtcatgtca    2160
acagaggaag cagagttcag ccatgaatgg acaaccggtg agtggaaggt ggaagtgaat    2220
tttgatagcg aagagattct actagattat gcatctcagg tggaatcaga ttggccgctt    2280
acacatggtc aattttctc tatttgccg atttatgatt caggtggata cttagagaaa      2340
gtgtatcaaa ctgctaaatc ggtagaagcc caaacgttcc acgatgcgat tgtgcccttt    2400
atcgtagaag agctgtttga atatgcaggc aaatggcgta atattcgtgt gcaaggaccg    2460
acaacatttc taccatcctt gactgtacag gtagcaatgg caggtgccat gttgattggt    2520
ctgcatcatc gcatctgtta tacgacgagc gcttcggtct taactgaagc agttaagcaa    2580
tcagatcttc cttcaggtta tgaccatctg tgccagttcg taatgtctgg tcaactttcc    2640
gactctgaga aacttctgga atcgctagag aatttctgga atgggattca ggagtggaca    2700
gaacgacacg gatatatagt ggatgtgtca aaacgcatac cattttgaac gatgacctct    2760
aataattgtt aatcatgttg gttacgtatt tattaacttc tcctagtatt agtaattatc    2820
atggctgtca tggcgcatta acggaataaa gggtgtgctt aaatcgggcc attttgcgta    2880
ataagaaaaa ggattaatta tgagcgaatt gaattaataa taaggtaata gatttacatt    2940
agaaaatgaa aggggatttt atgcgtgaga atgttacagt ctatcccggc attgccagtc    3000
ggggatatta aaaagagtat aggttttat tgggataaag taggtttcac tttggttcac    3060
catgaagatg gattcgcagt tctaatgtgt aatgaggttc ggattcatct atgggaggca    3120
agtgatgaag gctggcgcct cgtagtaatg attcaccggt ttgtacaggt gcggagtcgt    3180
ttattgctgg tactgctagt tgccgcattg aagtagaggg aattgatgaa ttatatcaac    3240
atattaagcc tttgggcatt ttgcaccca atacatcatt aaaagatcag tggtgggatg     3300
aacgagactt tgcagtaatt gatcccgaca acaatttgat tagcttttt caacaaataa     3360
aaagctaaaa tctattatta atctgttcag caatcgggcg cgattgctga ataaaagata    3420
cgagagacct ctcttgtatc ttttttattt tgagtggttt tgtccgttac actagaaaac    3480
cgaaagacaa taaaaatttt attcttgctg agtctggctt tcggtaagct agacaaaacg    3540
gacaaaataa aaattggcaa gggtttaaag gtggagattt tttgagtgat cttctcaaaa    3600
aatactacct gtcccttgct gattttaaa cgagcacgag agcaaaaccc ccctttgctg     3660
aggtggcaga gggcaggttt ttttgtttct ttttctcgt aaaaaaaaga aaggtcttaa     3720
aggttttatg gttttggtcg gcactgccgc gcctcgcaga gcacacactt tatgaatata    3780
aagtatagtg tgttatactt tacttggaag tggttgccgg aaagagcgaa aatgcctcac    3840
atttgtgcca cctaaaaagg agcgatttac atatgagtta tgcagtttgt agaatgcaaa    3900
aagtgaaatc agctggacta aaaggcatgc aatttcataa tcaaagagag cgaaaaagta    3960
gaacgaatga tgatattgac catgagcgaa cacgtgaaaa ttatgatttg aaaaatgata    4020
aaaatattga ttacaacgaa cgtgtcaaag aaattattga atcacaaaaa acaggtacaa    4080
gaaaaacgag gaaagatgct gttcttgtaa atgagttgct agtaacatct gaccgagatt    4140
tttttgagca actggatcct gataggtggt atgttttcgc ttgaactttt aaatacagcc    4200
```

-continued

```
attgaacata cggttgattt aataactgac aaacatcacc ctcttgctaa agcggccaag    4260
gacgctgccg ccggggctgt ttgcgttttt gccgtgattt cgtgtatcat tggtttactt    4320 attttttttgc caaagctgta atggctgaaa attcttacat ttatttttaca ttttttagaaa   4380 tgggcgtgaa aaaaagcgcg cgattatgta aaatataaag tgatagcggt accgagctca    4440
aaggaggtga aatgtacaca tgcaaaagtt actgtctctc ccatctaact tagtccagag    4500 cttttcatgaa ttagaaagag taaatcggac tgactggttt tgcacatccg acccggtcgg    4560
aaaaaagctt ggcagtggcg gtggcacatc atggctgctc gaggaatgct ataatgaata    4620
ctctgacggc gcaactttcg gagagtggct cgaaaaagag aaagaatac tgctccacgc     4680 cggtgggcag tcccgccgtt tgccgggtta cgctcctagt ggtaagatcc ttacgccggt    4740
cccagtattt cgctgggaaa gaggacagca cctgggccag aaccttttga gtttacagct    4800
tccactttat gagaaaataa tgagcttagc tcctgacaag cttcataccc ttatcgccag    4860
cggagatgtc tatatacgct ctgaaaaacc gttgcagtcc atacctgagg ccgacgttgt    4920
ttgttacggg ctgtgggtcg acccttcctt ggcgacgcac catgggtat tcgccagtga    4980 ccgcaaacat ccggagcagc tcgacttcat gctccagaag ccttctttgg cagaacttga    5040
aagtctctct aagactcatc ttttcctgat ggacataggg atttggttat tgtccgatcg    5100
cgcggtagag attttgatga agcggtccca taaggagtcc tctgaagaat tgaaatacta    5160
tgatctttac agcgactttg ggcttgccct gggcacccac ccacggatag aagatgagga    5220
agtgaatact ctctcagttg caattctgcc tctcccgggc ggggagtttt atcattacgg    5280
tactagcaaa gagctgattt cctccaccct gtcagtccag aataaggttt atgaccaacg    5340
ccggatcatg catagaaagg tcaaaccgaa ccctgccatg tttgtccaaa atgcggtagt    5400
acgtatccca ctgtgcgctg agaacgcaga cctctggatt gaaaactcac atataggtcc    5460
gaagtggaag atagcgagcc ggcatattat tactggggtg ccggagaacg actggagttt    5520
agcagtgcca gcagggtat gtgtcgacgt tgtcccgatg ggtgataaag gttttgtggc     5580
acggccttac gggctggacg atgtatttaa aggagacctg agagattcaa aaaccacttt    5640
gaccggaatc ccattcggtg aatggatgtc caaacgggga ctctcctaca ctgatctgaa    5700
aggtcggact gacgaccttc aagccgtgag cgtgtttccg atggtcaatt ccgttgagga    5760
attgggcctc gtactccgct ggatgctttc agaacctgag ttggaagagg gtaagaacat    5820
ctggcttcgc tccgagcact tctctgcgga tgaaataagc gctggagcga acctgaagcg    5880
cctctatgct caacgggaag aattccggaa ggggaactgg aaagcattag ccgttaacca    5940
tgagaagtcc gtattttacc aactcgattt ggccgatgcg gcggaggatt tcgtacggtt    6000
gggactcgac atgcctgaat tactccctga ggacgccctg cagatgagtc gcatccataa    6060
tagaatgctt cgcgctcgca tcctcaagct cgacggcaaa gattaccggc ctgaggaaca    6120
ggcagcgttc gatctgctgc gcgacggttt gctcgatgga atctctaacc gtaaaagcac    6180
accaaagctg gacgtttatt ctgaccaaat agtgtggggc cggagcccag tacggattga    6240
tatggccggc ggctggaccg acacccccacc ttatagctta tattccggag gcaatgttgt    6300
gaaccttgcg attgaattaa atggtcaacc tccattgcag gtatacgtta agccgtgtaa    6360
ggacttccat atcgtcctgc ggtccattga catgggggct atggagatag tctcaacttt    6420
tgacgagctg caagactaca aaaagatcgg ttccccgttt tccataccaa agccgctct    6480 ctctcttgct ggattcgccc cggcatttag cgctgtgtca tatgcatcat tggaggaaca    6540
```

```
gttgaaagat tttggagctg gtattgaggt tacgttatta gccgccattc cggctggttc   6600
tggtcttggt acatcatcaa tactggcttc cacagtgctc ggggcaatta atgattttg    6660 tggactcgca tgggacaaaa atgaaatttg tcagagaaca ttagttttag agcaactgct   6720
gactacggga ggaggctggc aggaccagta cggcggggtc ttgcaaggtg ttaagcttct   6780
gcagaccgag gccgggttcg cgcaatcccc attagttaga tggctgccag accacctctt   6840
tacgcaccct gaatacaagg actgccattt gttatattac acaggaatta cgcgtacggc   6900
aaagggaata ctggcggaga tcgtctctag catgtttctc aatagtagcc tgcacctgaa   6960
tttactctca gaaatgaaag cgcatgccct cgacatgaac gaggctatac agcgcggctc   7020 cttttgttgag ttcggtcgcc ttgtcggaaa gacatgggag caaaacaagg cactcgacag  7080
tggtaccaac ccaccagcag tcgaagccat aatcgactta attaaggatt atacattagg   7140
gtataaactc ccaggggctg gaggaggcgg gtacctctac atggttgcta aagatccgca   7200
ggcagcagtg cgcatccgca aaattttaac agagaacgcg ccaaaccctc gtgcccggtt   7260
tgtggaaatg actctgtccg acaaaggctt tcaagtaagt cggtcctaaa ctagtgattg   7320
ctagctctag actgcagaag cttggcgtaa tcatggtcat agctgtttcc tgtgtgaaat   7380
tgttatccgc tcacaattcc acacaacata cgagccggaa gcataaagtg taaagcctgg   7440
ggtgcctaat gagtgagcta actcacatta attgcgttgc gctcactgcc cgctttccag   7500
tcgggaaacc tgtcgtgcca gctgcattaa tgaatcggcc aacgcgcggg gagaggcggt   7560
ttgcgtattg ggcgctcttc cgcttcctcg ctcactgact cgctgcgctc ggtcgttcgg   7620
ctgcggcgag cggtatcagc tcactcaaag gcggtaatac ggttatccac agaatcaggg   7680
gataacgcag gaaagaacat gtgagcaaaa ggccagcaaa aggccaggaa ccgtaaaaag   7740
gccgcgttgc tggcgttttt ccataggctc cgcccccctg acgagcatca caaaaatcga   7800
cgctcaagtc agaggtggcg aaacccgaca ggactataaa gataccaggc gtttccccct   7860
ggaagctccc tcgtgcgctc tcctgttccg accctgccgc ttaccggata cctgtccgcc   7920
tttctccctt cgggaagcgt ggcgctttct catagctcac gctgtaggta tctcagttcg   7980
gtgtaggtcg ttcgctccaa gctgggctgt gtgcacgaac cccccgttca gcccgaccgc   8040
tgcgccttat ccggtaacta tcgtcttgag tccaacccgg taagacacga cttatcgcca   8100
ctggcagcag ccactggtaa caggattagc agagcgaggt atgtaggcgg tgctacagag   8160
ttcttgaagt ggtggcctaa ctacggctac actagaagaa cagtatttgg tatctgcgct   8220
ctgctgaagc cagttacctt cggaaaaaga gttggtagct cttgatccgg caaacaaacc   8280
accgctggta gcggtggttt ttttgtttgc aagcagcaga ttacgcgcag aaaaaaagga   8340
tctcaagaag atcctttgat cttttctacg ggtctgacg ctcagtggaa cgaaaactca   8400
cgttaaggga ttttggtcat gagattatca aaaaggatct tcacctagat ccttttaaat   8460
taaaaatgaa gttttaaatc aatctaaagt atatatgagt aaacttggtc tgacagttac   8520
caatgcttaa tcagtgaggc acctatctca gcgatctgtc tatttcgttc atccatagtt   8580
gcctgactcc ccgtcgtgta gataactacg atacgggagg gcttaccatc tggccccagt   8640
gctgcaatga taccgcgaga cccacgctca ccggctccag atttatcagc aataaaccag   8700
ccagccggaa gggccgagcg cagaagtggt cctgcaactt tatccgcctc catccagtct   8760
attaattgtt gccgggaagc tagagtaagt agttcgccag ttaatagttt gcgcaacgtt   8820
gttgccattg ctacaggcat cgtggtgtca cgctcgtcgt ttggtatggc ttcattcagc   8880
tccggttccc aacgatcaag gcgagttaca tgatccccca tgttgtgcaa aaaagcggtt   8940
```

```
agctccttcg gtcctccgat cgttgtcaga agtaagttgg ccgcagtgtt atcactcatg    9000
gttatggcag cactgcataa ttctcttact gtcatgccat ccgtaagatg cttttctgtg    9060
actggtgagt actcaaccaa gtcattctga gaatagtgta tgcggcgacc gagttgctct    9120
tgcccggcgt caatacggga taataccgcg ccacatagca gaactttaaa agtgctcatc    9180
attggaaaac gttcttcggg gcgaaaactc tcaaggatct taccgctgtt gagatccagt    9240
tcgatgtaac ccactcgtgc acccaactga tcttcagcat ctttactttt caccagcgtt    9300
tctgggtgag caaaaacagg aaggcaaaat gccgcaaaaa agggaataag ggcgacacgg    9360
aaatgttgaa tactcatact cttccttttt caatattatt gaagcattta tcagggttat    9420
tgtctcatga gcggatacat atttgaatgt atttagaaaa ataaacaaat aggggttccg    9480
cgcacatttc cccgaaaagt gccacctgac gtctaagaaa ccattattat catgacatta    9540
acctataaaa ataggcgtat cacgaggccc tttcgtc                             9577

<210> SEQ ID NO 4
<211> LENGTH: 615
<212> TYPE: DNA
<213> ORGANISM: Artificial Sequence
<220> FEATURE:
<223> OTHER INFORMATION: Synthetic DNA

<400> SEQUENCE: 4
atgaaagaaa gagggttatt aatcgttctc tcaggtccct caggagttgg taaaggaacg      60
gttcgacaag cgatcttttc gcaggaagac acaaaatttg aatattcgat ttcagtaacc     120
acaagaagtc caagagaggg cgaagtgaac ggagtcgatt attttttcaa aacaagagac     180
gaattcgagc aaatgattgc ggacaacaag ctgcttgaat gggcagagta tgtcggcaat     240
tattacggca cgccagtcga ttatgttgaa cagacgcttc aagatggaaa agacgtcttt     300
ttagaaattg aagttcaagg ggctcttcaa gtgagaaatg cttccccgga aggcctgttt     360
attttccttg cgcctccaag cctttctgaa ctgaaaaaca gaatcgtgac acgaggaaca     420
gaaacagacg ctctgattga aaatcgaatg aaagccgcaa aagctgagat cgaaatgatg     480
gatgcttatg actatgtcgt tgaaaacgat aatgtcgaaa cggcttgcga taaaatcaaa     540
gcaatcgttc ttgctgaaca tttgaagcgt gaacgcgttg caccaagata taagaaaatg     600
ctggaggttg aataa                                                     615

<210> SEQ ID NO 5
<211> LENGTH: 450
<212> TYPE: DNA
<213> ORGANISM: Artificial Sequence
<220> FEATURE:
<223> OTHER INFORMATION: Synthetic DNA

<400> SEQUENCE: 5
atgatggaaa agactttat catggtgaaa ccagacggtg tccaacgtca gctcattggg      60 gacatttat ctagattcga acgtaagggc ttacaattag ctggcgccaa gttaatgaga     120
gtgactgaac aaatggctga gaaacactac gccgaacatc aaggtaagcc tttcttcgga     180
gagctcgttg agtttattac ttcaggacct gtattcgcaa tggtgtggga aggcgaaaat     240
gtcattgaag tgacgagaca gctgatcggg aaaacaaacc ctaaagaagc tttacctggt     300
```

```
acgattcgtg gggattatgg catgtttgtc ggaaaaaaca tcatccacgg ctctgattct    360
ctcgaaagtg cagaacgcga gattaacatt ttctttaaga atgaagaatt agtatcatat    420
cagcagctta tggcaggctg gatctattaa                                     450
```